(12) United States Patent
Chew et al.

(10) Patent No.: US 8,211,307 B2
(45) Date of Patent: Jul. 3, 2012

(54) METHOD AND APPARATUS FOR PROCESSING ALGAE

(75) Inventors: Geoffrey Chew, Huntsville, AL (US);
Alton J. Reich, Huntsville, AL (US); H. Waite H. Dykes, Jr., Huntsville, AL (US); Roberto Di Salvo, Madison, AL (US)

(73) Assignee: Streamline Automation, LLC, Huntsville, AL (US)

( * ) Notice: Subject to any disclaimer, the term of this patent is extended or adjusted under 35 U.S.C. 154(b) by 0 days.

(21) Appl. No.: 13/083,844

(22) Filed: Apr. 11, 2011

(65) Prior Publication Data

US 2011/0192792 A1 Aug. 11, 2011

Related U.S. Application Data

(63) Continuation-in-part of application No. 12/970,512, filed on Dec. 16, 2010, and a continuation-in-part of application No. 12/970,484, filed on Dec. 16, 2010.

(51) Int. Cl.
*B01D 11/02* (2006.01)
*C12N 1/12* (2006.01)

(52) U.S. Cl. ...... 210/634; 210/638; 210/639; 435/257.1
(58) Field of Classification Search .......................... None
See application file for complete search history.

(56) References Cited

U.S. PATENT DOCUMENTS

| | | | |
|---|---|---|---|
| 4,341,038 A | 7/1982 | Bloch et al. | |
| 7,300,585 B1* | 11/2007 | Holzwarth et al. | 210/666 |
| 2004/0198849 A1* | 10/2004 | Aminabhavi et al. | 521/27 |
| 2006/0141556 A1 | 6/2006 | Jeong et al. | |
| 2006/0241287 A1 | 10/2006 | Hecht et al. | |
| 2008/0090284 A1 | 4/2008 | Hazlebeck et al. | |
| 2009/0071064 A1 | 3/2009 | Machacek et al. | |
| 2009/0170184 A1 | 7/2009 | Shepherd et al. | |
| 2009/0234146 A1 | 9/2009 | Cooney et al. | |

FOREIGN PATENT DOCUMENTS

| WO | WO0160166 | 8/2001 |
|---|---|---|
| WO | WO2010023136 | 3/2010 |

OTHER PUBLICATIONS

Gutowski et al. Controlling the aqueous miscibility of ionic liquids: Aqueous biphasic systems of water-miscible ionic liquids and water-structuring salts for recycle, metathesis, and separations. J. Am. Chem. Soc. vol. 125 (2003) 6632-6633.*

* cited by examiner

*Primary Examiner* — Krishnan S Menon
*Assistant Examiner* — Katherine Zalasky
(74) *Attorney, Agent, or Firm* — KIPA AB; Tomas Friend

(57) ABSTRACT

Methods and apparatus for processing algae are described in which a hydrophilic ionic liquid is used to lyse algae cells. The lysate separates into at least two layers including a lipid-containing hydrophobic layer and an ionic liquid-containing hydrophilic layer. A salt or salt solution may be used to remove water from the ionic liquid-containing layer before the ionic liquid is reused. The used salt may also be dried and/or concentrated and reused. The method can operate at relatively low lysis, processing, and recycling temperatures, which minimizes the environmental impact of algae processing while providing reusable biofuels and other useful products.

20 Claims, 5 Drawing Sheets

METHOD AND APPARATUS FOR PROCESSING ALGAE

CROSS-REFERENCE TO RELATED APPLICATIONS

This application claims priority under 35 U.S.C. 120 to the following U.S. patent applications, which are incorporated by reference in their entirety: Ser. No. 12/970,484, filed Dec. 16, 2010 and Ser. No. 12/970,512, filed Dec. 16, 2010, and which claims priority to 61/358,322 filed Jun. 24, 2010.

FEDERALLY SPONSORED RESEARCH OR DEVELOPMENT

The United States Government may have certain rights to the invention pursuant to Contract Number DE-SC0001306 awarded by the U.S. Department of Energy.

BACKGROUND OF THE INVENTION

1. Field of the Invention

The present invention relates to methods, compositions, and apparatus used to process algae and thereby extract various products such as lipids, proteins, carbohydrates, metabolites, and/or recombinant products from algae.

2. Description of Related Art

Algae, including microalgae, macroalgae, fresh water algae, and marine algae are potentially useful as sources of industrial, agricultural, and pharmaceutical products and their precursors.

WO 2001/060166 A1 discloses fermentation, lysis, and extraction of docosahexaenoic acid (DHA) from the marine algae *Cypthecodinium cohnii* and the potential use of macroalgae such as *Rhodophyceae, Gigartinaceae, Gigartina stellata*, and *Chondrus crispus* as sources of carrageenan and DHA for pet food. The non-used remains of the algae are combined with yeast in a process for making pet treats.

U.S. 2006/0241287 A1 discloses a method for using ionic liquids to extract and separate a biopolymer from a biomass. The biopolymer is dissolved in the ionic liquid and may then be separated from the ionic liquid. The process, and therefore the biomass, must take place in the substantial absence of water. Algae is cited in the publication as a suitable biomass source for chitin but no example of chitin extraction from algae biomass is provided and no conditions related to chitin extraction are suggested. The publication does not describe the extraction of lipids or materials other than biopolymers from biomass or the extraction of any substances from wet algae or other wet biomass.

U.S. 2006/0141556 A1 discloses a cell lysis method using microwaves in which an ionic compound additive, which may be an ionic liquid, is used to increase the efficiency of microwave heating during a cell lysis step to prepare nucleic acid for subsequent PCR. Organic ionic liquids such as dialkylimidazolium salts are suggested as potentially useful for the method. The amount of ionic additive used in approximately 10% by weight in the sample to be lysed and this amount is confirmed as insufficient to cause cell lysis.

U.S. 2008/0090284 A1 discloses a system for processing oil from algae. The system comprises an algae separator, a cell lysis device, an oil separator, and a biofuel reactor. No specific means of cell lysis is suggested nor is a suggestion regarding chemical vs. mechanical lysis provided.

U.S. 2009/0081742 discloses a method for processing algae in which steam is used to lyse algae cells. The system includes a bioreactor for synthesizing biodiesel from intracellular oil. The lysing process involves the mixture of steam with a concentrate of algae cells.

U.S. 2009/0170184 A1 discloses a system for growing and processing algae. The system comprises bioreactors for growing algae, a dewatering unit for concentrating algae, a cell lysis chamber, and a separator for separating lysis products. Algae cells in the lysis chamber are mixed with $CO_2$ at a pressure greater than 1 bar. Pressure/phase changes of CO2 injected into the algae cells are used to rupture the cells.

U.S. 2009/0234146 A1 discloses methods for the direct transesterification and extraction of biolipids from biomass, including plants, yeast, and algae. Large numbers of possible ionic liquid/cosolvent combinations are suggested. All examples of the process involve drying the biomass and grinding it into a fine powder.

WO 2010/023136 ('136) discloses a process for producing liquid fuels from lipid-containing biomass, including algae, by: (i) providing the biomass in a dry or semi-dry form and (ii) dissolving said the biomass in an ionic liquid at a temperature of between 60° C. and 120° C. whereby a lipid phase and a hydrophilic phase are formed. The hydrophilic phase may contain cellulose, hemi-cellulose and dissolved protein. The ionic liquids are selected from a large number of organic or inorganic salts having melting temperatures of about 120° C. or less and include imidazolium cations combined with halides, C1-C6 carboxylates, C1-C6 alkyl sulfates, mono-and di-C1-C10 alkyl sulfosuccinates, mono- and di-C1-C10 ester sulfosuccinates, and mixtures thereof. Inorganic ionic liquids are preferred with $ZnCl_2 \cdot xH_2O$, x>2 most preferred, in part because biomass proteins in non-denatured (natural) form are soluble in the ionic liquid medium. The '136 publication does not exemplify the lysis method or disclose critical conditions such as durations of lysis and relative amounts of ionic liquid and biomass. No correlations are made between ionic liquids, algae, and conditions for lysis.

The aforementioned processes do not meet the need for an environmentally safe and economically viable process for producing biofuels, nutrients, and other useful products from algae biomass. Lysing algae by steam, microwaves, and mechanically induced pressure changes require relatively large amounts of energy. Chemical lysis methods often involve volatile organic chemicals or ionic detergents that interfere with subsequent separations. Drying algae to a powder requires energy for centrifugation, filtering, and/or heating. High temperatures during lysis and drying can denature proteins or degrade other desirable products. Unlike biomass obtained on land, harvested algae contains a large percentage of water. The present specification discloses methods and apparatus involving the use of certain hydrophilic ionic liquids to lyse algae cells. The ionic liquids and conditions disclosed are distinct from those useful for dissolving and/or processing dry biomass.

Lysis and extraction of algae cells by ionic liquids can provide an environmentally sound alternative to more energy intensive methods, but they are expensive and have only recently been shown to lyse wet algae concentrates at temperatures as low as 80° C. U.S. patent application Ser. No. 12/970,512, assigned to the same assignee as the present application, discloses the use of ionic liquid 1-butyl-3-methylimidazolium chloride to lyse suspensions of algae cells at temperatures of approximately 80° C. to 120° C. and to extract lipids from the resulting lysate. The lysate may also be processed to recover other materials from the algae. The ionic liquid is recovered for re-use by the addition of a salt to salt-out algal components and water.

The present invention provides methods and apparatus for processing algae at ambient or elevated temperatures using ionic liquids, efficient recovery of ionic liquid using a salting-out procedure, and recycling of salts and ionic liquid. The process ay be used to isolate a wide variety of materials from algae for use in biofuels, pharmaceuticals, nutraceuticals, foods, and other products.

BRIEF SUMMARY OF THE INVENTION

The present invention provides methods and apparatus for separating various components of micro- and macro-algae to produce biofuels, nutrients, pharmaceuticals, and/or their precursors. The process comprises lysing wet algal concentrates with a hydrophilic ionic liquid (IL), separation of the lysate into at least two immiscible phases, and recovery of the IL for reuse. Lysis may be performed at ambient temperatures or elevated temperatures but below temperatures at which the IL experiences substantial chemical degradation.

DETAILED DESCRIPTION OF THE INVENTION

The present invention results, in part, from a number of discoveries related to the relative abilities of ILs to lyse microalgae and macroalgae cells; the conditions required for ionic liquid lysis of cells, and the separation of cell lysate products.

Figure 1:
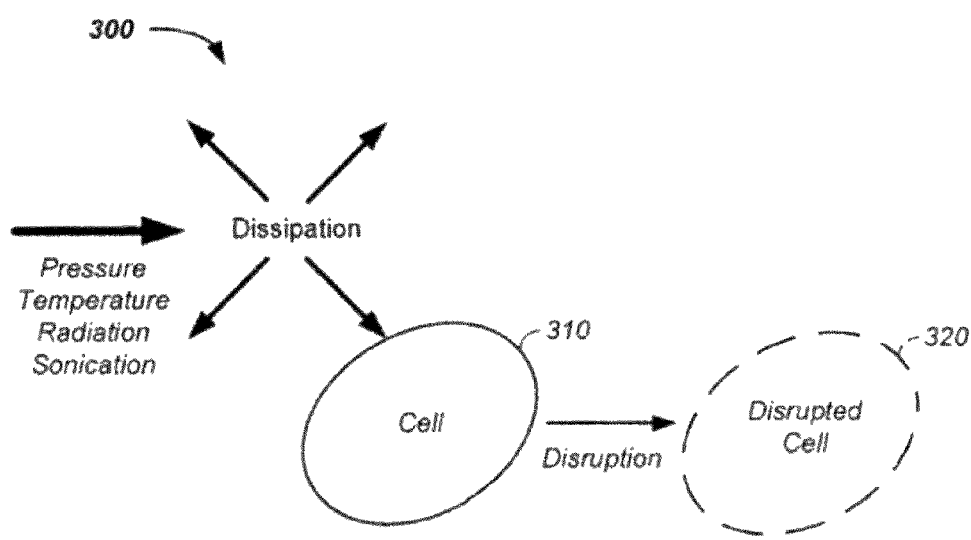
FIG. 1 is a drawing depicting cell disruption and cell lysis.
Figure 1:
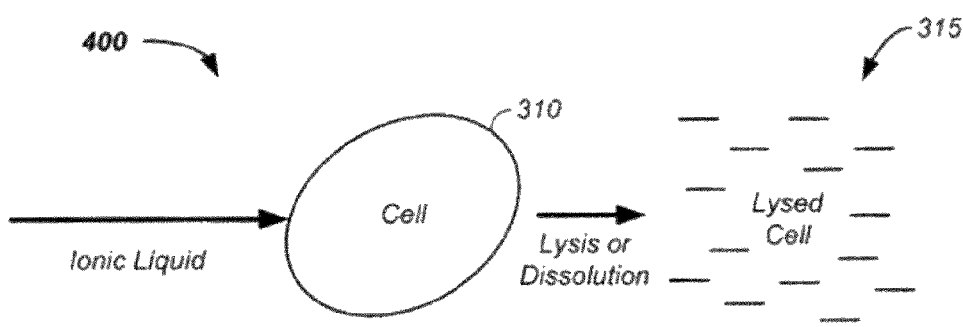

The term "lysis" is generally used to describe processes for breaking open cells so that their contents spill out of the cells. These processes may involve the rupturing of cell membranes and walls without dissolving them (disruption) or the dissolution of cell membrane and cell wall components. The processes are illustrated in FIG. 1. Disruption 300 refers to a process in which the plasma membrane and cell wall 310 are perforated or torn apart without entirely dissolving the lipid bilayers and/or cell wall and may produce disrupted cellular shells, or ghosts 320. Lysis 400 of algae cell involves the dissolution of the cell membrane and cell wall 310 and may result in the formation of dissolved cellular components 315 that may be present as a mixture of hydrophobic and hydrophilic components. Pressure, sonication, microwaves, and high temperature are often used to disrupt cells while detergents and solvents are often used to dissolve cell membranes. Some cellular components may remain associated with cell membranes and cell walls after disruption but not after lysis.

Normally, cell lysis and extraction by chemical means involves the use of two immiscible solvent phases with one solvent being hydrophilic for dissolving water soluble molecules from the lysate and the other solvent being hydrophobic to dissolve cell membranes and lipophilic molecules from the cell lysate. Materials that are insoluble in either solvent are removed, for example, by filtration, centrifugation, or settling.

The present method involves the lysis of algal cell suspensions or cells in whole or shredded macroalgae with a hydrophilic IL in a lysing reactor. Algae cells and IL are mixed in the lysing reactor for a duration of 60 min. or less, 30 min. or less, 10 min. or less, or 5 min. or less but sufficient to produce a cell lysate. The temperatures of the cells and/or IL may be controlled before mixing and/or the temperature of the mixture may be controlled. Lysis my be performed, for example, at a temperature of 105° C. or less, 80° C. or less, 70° C. or less, 50° C., 40° C., or 25° C. or less. The lysing reactor may comprise a vessel or tank with agitation means for mixing the IL and algae cells and/or a pipe in which mixing of the IL and algae cells is achieved by turbulent flow of the IL and algae mixture through the pipe.

Figure 2:
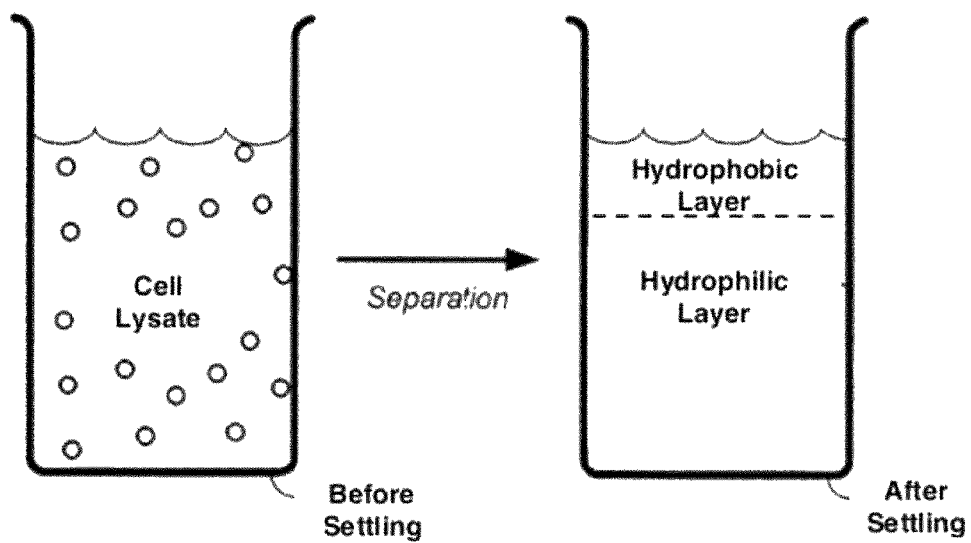
FIG. 2 is a diagram showing separation of cell lysate phases.
Figure 3:
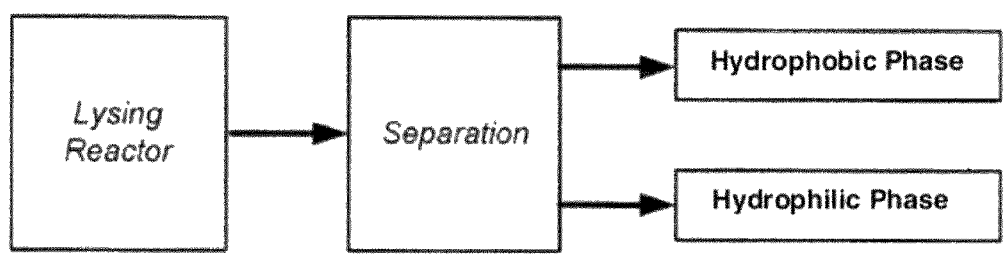
FIG. 3 is a diagram showing a lysing reactor and separation chamber.
Figure 5:
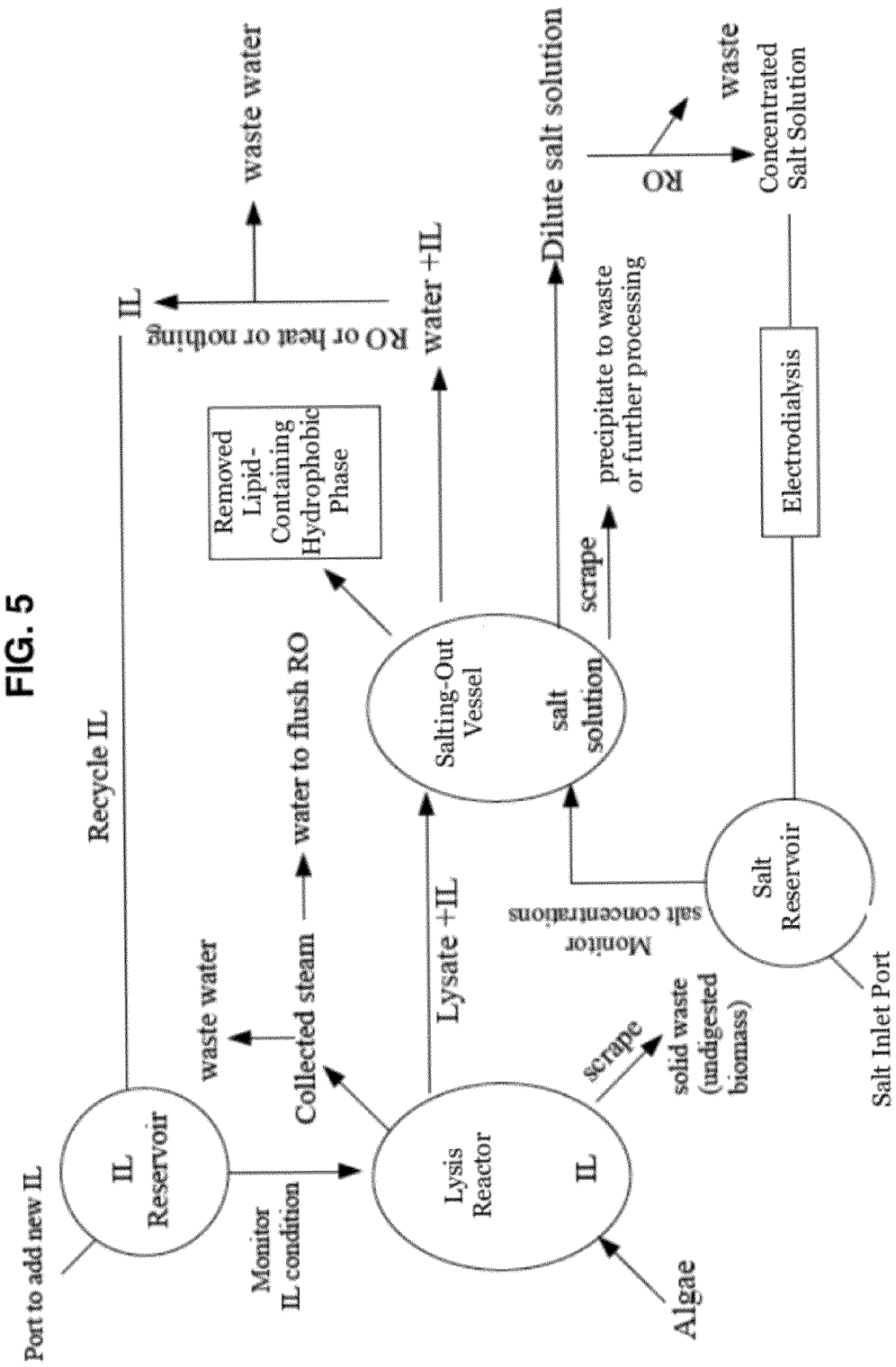
FIG. 5 is a diagram of one embodiment of method and apparatus for processing algae.

The cell lysate may be transferred to a separation chamber in which at least two immiscible liquid layers form: a hydrophilic layer comprising the IL and dissolved hydrophilic components of the lysate such as starch and water-soluble proteins, carbohydrates, glycerol, and metabolites; and a hydrophobic layer comprising lipid components from the cell lysate such as triacylglycerols, fatty acids, ubiquinone, and lipid-soluble metabolites (FIG. 2). Alternatively, the lysing chamber and separation chamber may be one and the same. The hydrophobic layer normally has a lower density and smaller volume than the hydrophilic layer. The two layers may be allowed to separate through the force of gravity or separation may be accelerated, for example by centrifugation. The upper, hydrophobic lipid layer is removed from the separated cell lysate and processed (FIGS. 3 and 5). Undissolved solids, such as silicates, generally separate under the force of gravity to form a layer of solids that is more dense than the hydrophilic layer and may be separated from the hydrophilic layer, or phase, for example, by removing the hydrophilic layer from the container holding the lysate (FIG. 5). In some cases, a precipitate may form at the interface between the hydrophobic and hydrophilic layers and may be removed before or after the removal of one or more of the hydrophobic and hydrophilic layers (phases).

Figure 4:
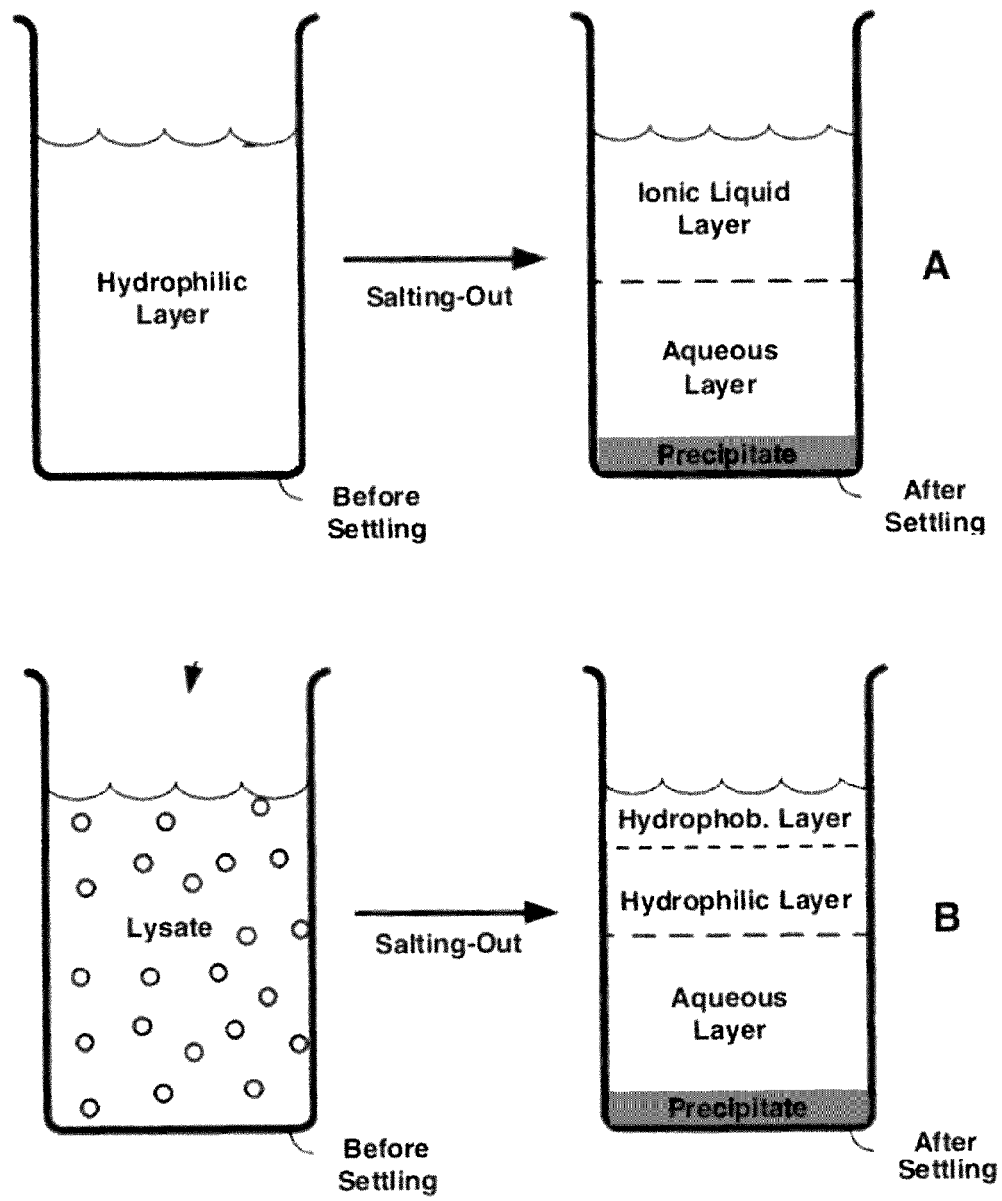
FIGS. 4A and B show alternative phase separations during a salting-out step.

Once the lipid-containing hydrophobic layer is removed, the IL may be recovered for reuse by the addition of a salt, preferably a kosmotropic salt and most preferably $K_3PO_4$, in a salting-out vessel. The addition of salt effectively draws water from the hydrophilic IL and results in the formation of at least two phases, or layers: an IL layer comprising the IL and an aqueous layer comprising an aqueous solution of the salt (FIG. 4A). The aqueous solution may also contain proteins, carbohydrates, and other cell components that precipitate as the salt concentration rises with added salt. This means that the stepwise addition of salt may be used to sequentially salt out different fractions of cellular constituents, if desired. If a sufficient amount of salt is added, a solid layer, or phase, of precipitate forms at the bottom of the salting-out vessel and/or the boundary between the aqueous phase and the IL phase. A precipitate at the bottom of the salting-out vessel may be recovered before or preferably after the IL and aqueous layers are removed. A precipitate at the interface between the IL and aqueous phases may be recovered before or preferably after one of the IL and aqueous layers is removed. A number of salting-out vessels may be used for sequential fractionation with the IL from each vessel being recovered for reuse in the lysing reactor.

Salting-out of the IL may also take place before the separation of the hydrophobic and hydrophilic phases of the cell lysate (FIG. 4B). For example, salt may be added the cell lysate, which is then allowed to settle in a salting-out vessel to form at least three immiscible liquid layers: a hyrdophobic, lipid-containing layer, an IL layer, and an aqueous salt solution layer. The lipid-containing layer, or phase, generally has the lowest density of the three phases and forms the top layer.

The aqueous salt solution is normally the most dense and forms the bottom liquid layer, or phase after settling. Salting-out may be performed using a single or sequential addition of salt. In addition to the liquid phases, precipitates may form and collect at the bottom of the vessel and/or one or more the boundaries between the liquid phases.

The ability of the hydrophilic IL to lyse cells is dependent on the ratio of IL to water. Lower IL to water ratios are associated with less cell lysis. Water may be removed from the IL by salting out or, alternatively, by heating with passive or active solar heat, microwaves, or heat from combustion. The salt used may be recycled by allowing water to evaporate from the salt in open pools, for example, or by active or passive solar heating, or reverse osmosis to remove water. Heat may also be provided by burning of dried biomass or its decomposition products. Recycling of the IL and salt provides for minimal impact on the environment. The relatively low temperatures required for lysis and drying of salt and optionally IL provide advantages over existing algae processing methods both environmentally and economically.

Ionic Liquids:

The inventors have discovered that a series of hydrophilic ILs lyse algae cells in a temperature range of from less than 20° C. to greater than 105° C. The ability to lyse algae at lower temperatures reduces the amount of energy required for algae cell processing and reduces or prevents thermal degradation of the ILs. The inventors have observed complete cell lysis and essentially complete lysis in which trace amounts of undissolved cellular components and/or extracellular material are observed. In practice, the process need not necessarily involve complete lysis or even essentially complete lysis. In some instances, it may be economically advantageous to use the present invention under conditions in which for example, only 80% or 90% of the algae cells are lysed. This may be the case, for example, if the difference in the cost of performing the method under conditions resulting in the lysis of 100% of cells and 80% or 90% of the cells is greater than the difference in the corresponding profits obtained.

At 105° C., 1-ethyl-3-methylimidazolium acetate ([EMIM]Ac), 1-ethyl-3-methylimidazolium chloride ([EMIM]Cl), 1-butyl-3-methylimidazolium chloride ([BMIM]Cl), 1-methyl-3-octylimidazolium chloride ([OMIM]Cl), 1-Hexyl-3-methylimidazolium chloride ([HMIM]Cl), and 1-Hexyl-3-methylimidazolium iodide ([HMIM]I) completely lyse suspensions of the microalgae *Chlorella vulgaris* having concentrations lower than 20% by weight within 60 min. and at a ratio of 20:1 IL:algae suspension. Under the same conditions, 1-methyl-3-octylimidazolium bis(trifluromethylsulfonyl)imide ([OMIM]TFSI), 1-hexyl-3-methylimidazolium bis(trifluromethylsulfonyl) imide ([HMIM]TSFI), 1-methyl-3-octylimidazolium hexafluorophosphate ([OMIM]$PF_6$), 1-hexyl-3-methylimidazolium hexafluorophosphate ([HMIM]$PF_6$), 1-methyl-3-octylimidazolium tetrafluoroborate ([OMIM]$BF_4$), and 1-hexyl-3-methylimidazolium tetrafluoroborate ([HMIM]$BF_4$) do not completely lyse *Chlorella vulgaris*.

At 70° C., [EMIM]Ac completely lyses a 20% by weight algae suspensions in 15 min. at a 10:1 ratio of IL to algae suspension (biomass) and in 5 min. at a 15:1 ratio of IL to algae suspension. [EMIM]Ac completely lyses a 20% by weight aqueous suspension *Nannochloropsis oculata* within 30 min. at 70° C. at 10:1, 15:1, and 20:1 ratios of IL to algae. [EMIM]Ac, [BMIM]Cl, [HMIM]Cl, [HMIM]I, and [OMIM]Cl completely lyse 20% by weight algae in water (biomass) at 70° C. in 15 min. using an IL:biomass ratio of 20:1.

At a temperature of 25° C., [EMIM]Ac completely lyses a 20% by weight aqueous suspension *Nannochloropsis oculata* within 30 min. using 15:1 and 20:1 ratios of IL to algae with brief agitation. [EMIM]Ac completely lyses a 20% by weight aqueous suspension *Chlorella vulgaris* within 30 min. at 23° C. using a 15:1 ratio of IL:algae with brief agitation. At 23° C. and using an IL to biomass ratio of 20:1, [EMIM]Ac, [HMIM]Cl, [HMIM]I, and [OMIM]Cl are each capable of lysing approximately 70% of algae cells in a 20% by weight aqueous suspension.

[EMIM]Ac, [HMIM]Cl, [HMIM]I, and [OMIM]Cl are liquids at room temperature, [EMIM]Cl has a melting point of 87° C. and [BMIM]Cl has a melting point of 65° C. [EMIM]Ac, [HMIM]Cl, [HMIM]I, and [OMIM]Cl are therefore preferred for the lysis of algae at temperatures below 65° C. A mixture of ILs having a different melting point from the pure ILs used in the mixture may also be used for cell lysis. Blended mixtures of ILs may also have greater lysing activity than single ILs. For example, a mixed IL consisting of 50% [EMIM]OAc and 50% [BMIM]OAc by weight produces 100% lysis at room temperature (approximately 22° C.) in 15 min. using a mass ratio of 5:1 IL to 20% algae in water biomass.

The efficiency of lysis by ILs increases with temperature and decreasing water concentration. Keeping other conditions constant, the ratio of IL to algae suspension may be reduced as the water content of the algae suspension decreases (i.e. the algae cell concentration increases). It is also possible to further optimize lysis conditions including temperature, weight percent of algae in aqueous microalgae suspension or harvested macroalgae, IL composition, and IL:biomass ratio according to the species algae and product(s) to be isolated from the algae.

The present method has been practiced and functions with the following species of fresh water and marine algae: *Chlorella vulgaris*, *Chlorella pyrenoidosa*, *Chlorella Chlamydomonas reinhardtii*, *Chlamydomonas moewusii*, *Scenedesmus dimorphus*, *Selenastrum capricornotum*, *Chlorococcum* (various species), *Nannochloropsis oculata*, *Tetraselmis* (various species), *Sargassum muticum*, and *Laminaria digitata*. The present method, having been demonstrated with a variety of micro algae and macroalgae species, appears to be functional with algae in general.

Concentrated macroalgae, or wet algae, preparations of up to 95% by weight or higher can easily be produced from harvested macroalgae without the dewatering and concentrating steps required to produce equally concentrated suspensions of microalgae. [EMIM]Ac completely lyses cells in a blended (finely chopped) preparation of macroalgae *Sargassum muticum* at 105° C. and a 7:1 ratio of IL to algae (mass: mass).

Cooling of the lysate to 23° C. results in the formation of a precipitate containing cell wall components and precipitated proteins. Similar results are obtained with *Laminaria digitata* and an IL to algae ratio of 2:1. Blended *Laminaria digitata* cells are essentially completely dissolved when mixed with [EMIM]Ac at 23° C. for 2 hrs. at a ratio of 2:1 IL:algae (mass:mass), with undissolved material consisting of extracellular stem material. Whole macroalgae may also be mixed with IL in a lysis reactor for a time sufficient for the IL to extract lipid without completely dissolving the macroalgae or all macroalgae cells. Microalgae cell suspensions at concentrations of 80% to 95% by weight or higher and cells in wet macroalgae preparations can be essentially completely lysed at temperatures of between 23° C. and 105° C. using mass ratios of IL to (wet) algae of between 7:1 to 2:1 or 10:1 to 2:1. Macroalgae may not be completely lysed, for example, because macroalgae can contain extracellular components that are not completely dissolved by the IL. Undissolved material may be removed from the lysis reactor and/or the salting-out vessel by any suitable method including scraping, filtering, and/or centrifugation.

$K_3PO_4$ is preferred as a kosmotropic salt for removing water and solutes from the IL in the salting out process. Other salts that may be used include $K_3PO_4$, $K_2HPO_4$, $K_2SO_4$, $MgSO_4$, $Li_2SO_4$, $ZnSO_4$, $Al_2(SO_4)_3$, $Mg_3(PO_4)_2$, $Li3PO_4$, $Zn_3(PO_4)_2$, $ALPO_4$, $Na_2CO_3$, $(NH_4)_2SO_4$, $(NH_4)_2HPO_4$, and mixtures thereof. The salt may be added to a salting out vessel in the form of a solid or a solution, preferably a saturated or nearly saturated solution. The amount of salt required to remove water from the IL depends on the amount of water absorbed by the IL. For example, a saturated solution of $K_3PO_4$ may be added to a lysate or IL-containing hydrophilic phase in an amount sufficient to result in the formation of an IL phase and a salt solution phase. The IL phase may be reused for a subsequent round of cell lysis directly or it may be dried to remove any water remaining in the IL after salting-out. The kosmotropic salt solution may become contaminated by NaCl and other salts present in algae and seawater. Electrodialysis of contaminated kosmotropic salt solution may be used to separate the kospmotropic salt from contaminating salt(s).

FIG. 5 shows one embodiment of the method and apparatus for processing algae. A suspension of algae is mixed with IL in a lysis reactor. The algae is preferably dewatered to a predetermined mass of algae per liter in a range of from 0.1 to 1 kg/liter. If macroalgae is to be processed, the algae may be whole, ground, chopped, or shredded to increase its surface area. The ratio of IL to algae suspension depends on the IL, temperature, algae, and water content of the algae suspension used. For algae cell concentrations as low as 10% to 20% by weight the mass ratio of IL to cell suspension is preferably in the range of 20:1 to 5:1. For concentrations of algae cells as high as 95% by weight (e.g. dewatered microalgae and whole or chopped macroalgae), the mass ratio of IL to algae cells is preferably between 10:1 and 1:1. The temperature in the lysis reactor is preferably between 20° C. and 105° C. and more preferably between 20° C. and 70° C. The IL and algae suspension are mixed to form a cell lysate by agitation for a period of from 5 min. to 2 hrs., preferably between 5 min. and 30 min. Agitation is stopped and undigested/undissolved biomass is allowed to settle to the bottom of the lysis reactor where it is removed, for example, by scraping.

The lysate is transferred to a salting-out vessel and mixed with a concentrated salt solution and/or a solid salt. The salt solution is preferably a saturated, or nearly saturated, salt solution and may be as low as 50% saturated. Because solubility of the salt is normally temperature-dependent, the temperature of the salting-out vessel may be controlled and changed during the salting-out step. For example, lysate may enter at a temperature of 70° C. and mix with a salt solution at the same temperature that is not saturated but becomes saturated as the temperature of the lysate/salt mixture drops. The amount of salt added varies depending on the water content of the lysate and is sufficient to result in the formation of separate IL and salt solution phases. The salt-lysate mixture is allowed to sit without agitation at a temperature of between 20° C. and 70° C. for between 1 and 10 min. to allow the formation of a lipid-containing hydrophobic phase, an IL phase, an aqueous salt solution phase, and a precipitate. The lipid-containing hydrophobic phase is removed and optionally further processed. The IL phase is removed and stored in an IL reservoir for subsequent reuse in the lysis reactor. Any water remaining in the IL may optionally be removed, if necessary, by reverse osmosis (RO) or heating before transfer to the lysis reactor. The aqueous salt solution phase is removed from the salting-out vessel and concentrated by RO, heat, or natural evaporation, for example in a large surface area pool, before being stored in a salt solution reservoir. The salt solution reservoir preferably contains a salt inlet port for adding additional salt, if necessary, to maintain a desired salt concentration. The concentration of salt in the salt solution and water content and purity of the IL are preferably monitored and controlled. Precipitate from the salting-out vessel is removed by scraping, for example, and may be further processed, discarded, or dried and used as biomass fuel.

Lysis and separation may also be performed continuously in the lysis reactor by causing mixing to occur in a specific zone within the reactor where lysis occurs continuously. The contents of the cell lysate continuously move out of the mixing zone into regions within the vessel in which the IL is undisturbed and separate according to specific gravity. Mixing within the mixing zone may be driven by mechanical means or by injecting the microalgae cell suspension through nozzles and/or at flow velocities that induce mixing with the IL. The lysis reactor may alternatively be in the form of one or more pipes in which turbulent flow is used to mix IL and biomass.

Figure 6:
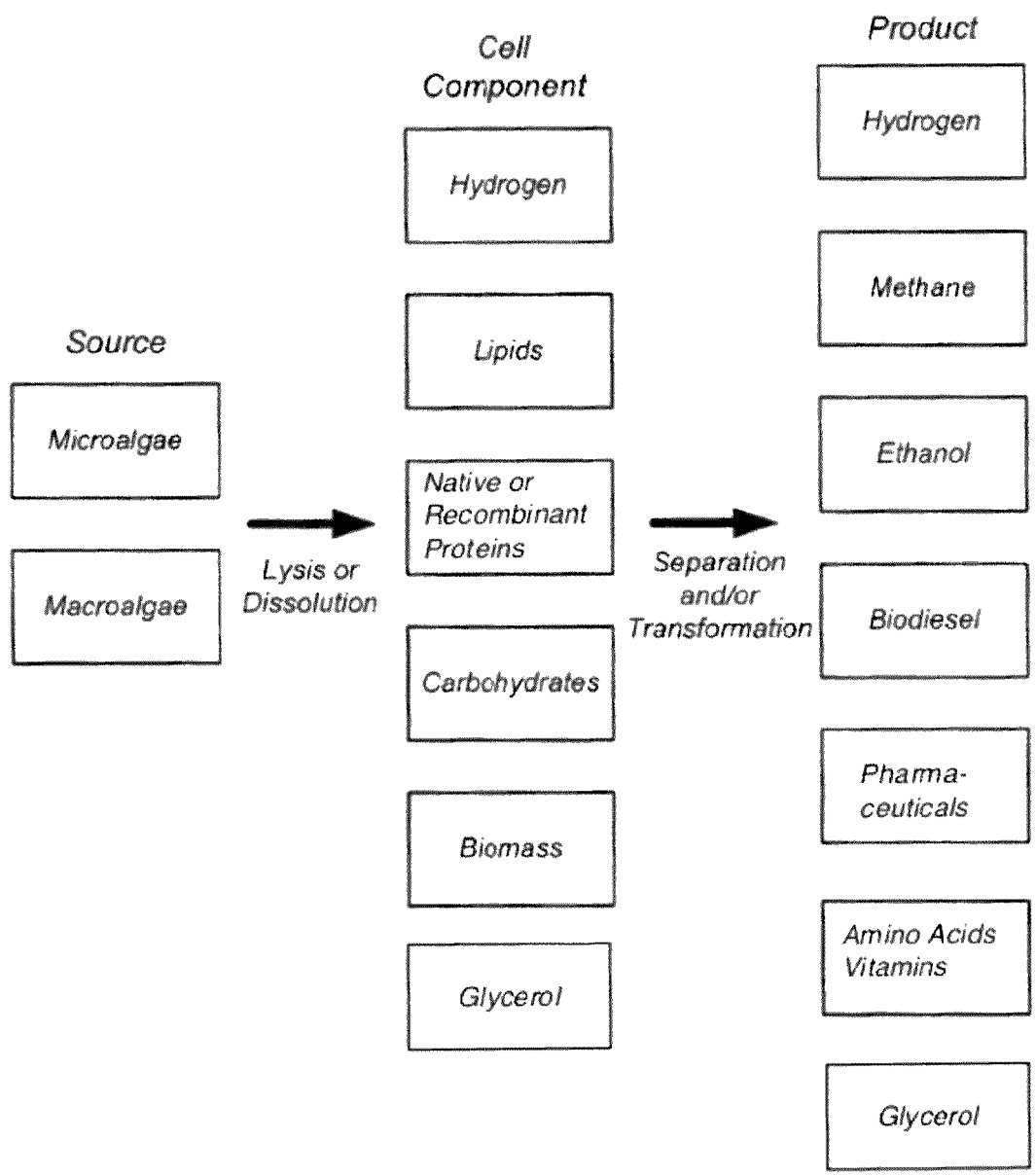
FIG. 6 is a flow diagram showing examples of cell components and resulting products.

It is also possible to add solid salt and/or concentrated salt solution to the salting-out vessel in a stepwise fashion and recovering precipitate after each addition of salt solution. In this way, precipitate fractions containing different species of proteins, for example, may be recovered separately to be processed different from one another. FIG. 6 illustrates some of the classes of constituents that can be extracted using the present process and some of the products to which they may be converted. Lipids such as triacylglycerols, fatty acids and diacylglycerols may be extracted for conversion to biodiesel and green diesel. Algae biomass may be converted to methane by anaerobic bacteria. Carbohydrates, proteins and metabolites can be processed into pharmaceuticals or nutrients by additional isolation, purification, and/or synthesis.

The invention has been described with reference to certain preferred embodiments. One of skill in the art will readily appreciate that other embodiments may be substituted for those described herein without departing from the spirit and scope of the invention.

What is claimed is:
1. A method for processing algae cells comprising the steps of:
 a) mixing an amount of wet algae cells with an amount of a hydrophilic ionic liquid-and thereby lysing at least 80% of said algae cells to produce a lysate, said lysate comprising at least 50% ionic liquid by weight;
 b) allowing the lysate to rest for a time sufficient for the formation of an ionic liquid-containing hydrophilic phase that is separate from a lipid-containing hydrophobic phase, said ionic liquid-containing hydrophilic phase comprising ionic liquid and water; and
 c) isolating the hydrophobic phase from the ionic liquid-containing hydrophilic phase to obtain a lipid-containing extract and an ionic liquid-containing hydrophilic extract from the algae cells.

2. The method of claim 1, and further comprising the steps of:
 d) mixing an amount of salt with the ionic liquid-containing hydrophilic extract isolated in step c); and
 e) allowing time sufficient for the formation of an aqueous salt solution phase that is separate from an ionic liquid phase.

3. The method of claim 2, wherein method steps d) and e) are repeated at least once.

4. The method of claim 2, and further comprising the step of:
   f) isolating the ionic liquid phase from the aqueous salt solution phase.

5. The method of claim 2, wherein:
   a precipitate is formed during one or both of steps d) and e) and
   during step e) the precipitate forms a layer and
   the method further comprising the step of isolating the precipitate.

6. The method of claim 3, wherein:
   a precipitate is formed during one or both of steps d) and e) and
   during step e) the precipitate forms a layer and
   the method further comprising the step of isolating the precipitate.

7. The method of claim 2, and further comprising the step of reusing the ionic liquid phase in a subsequent mixing step a).

8. The method of claim 7, and further comprising the step of drying the ionic liquid phase before its reuse in the subsequent mixing step a).

9. The method of claim 2, and further comprising the steps of removing water from the aqueous salt solution phase to form a concentrated salt solution and using said concentrated salt solution in a subsequent mixing step d).

10. The method of claim 9, and further comprising the step of performing electrodialysis on the aqueous salt solution phase and/or the concentrated salt solution.

11. The method of claim 1, wherein the algae cells are in the form of a water suspension of microalgae that contains approximately 0.1 kg to 1.0 kg algae cells per liter of cell suspension.

12. The method of claim 1, and further comprising the step of removing water from a culture of algae cells before mixing step a) so that the algae cells are present in an amount of approximately 0.1 kg to 1.0 kg algae cells per liter of cell suspension.

13. The method of claim 1, wherein the hydrophilic ionic liquid is selected from the group consisting of 1-ethyl-3-methylimidazolium acetate, 1-butyl-3-methylimidazolium chloride, 1-Methyl-3-octylimidazolium chloride, 1-Hexyl-3-methylimidazolium chloride, 1-Hexyl-3-methylimidazolium iodide and mixtures thereof.

14. The method of claim 1, wherein mixing step a) is performed at a temperature of 100° C. or lower.

15. The method of claim 1, wherein mixing step a) is performed at a temperature of 40° C. or lower.

16. The method of claim 1, wherein the ionic liquid and wet algae cells are present in a mass ratio of between 20:1 and 1:1 in mixing step a).

17. The method of claim 1, wherein the mass ratio of ionic liquid wet algae cells is between 10:1 and 2:1 and wet algae cells are present in a concentration of at least 80% by weight.

18. The method of claim 1, wherein the algae cells are selected from the group consisting of *Chlorella vulgaris, Chlorella pyrenoidosa, Chlorella ellipsoidea, Chlamydomonas reinhardtii, Chlamydomonas moewusii, Scenedesmus dimorphus, Selenastrum capricornotum, Chlorococcum* (various species), *Nannochloropsis oculata, Tetraselmis* (various species), *Sargassum muticum, Laminaria digitata*, and mixtures thereof.

19. The method of claim 2, wherein the salt is in the form of a solid and/or an aqueous salt solution containing a salt selected from the group consisting of $K_3PO_4$, $K_2HPO_4$, $K_2SO_4$, $MgSO_4$, $Li_2SO_4$, $ZnSO_4$, $Al_2(SO_4)_3$, $Mg_3(PO_4)_2$, $Li3PO_4$, $Zn_3(PO_4)_2$, $ALPO_4$, $Na_2CO_3$, $(NH_4)_2SO_4$, $(NH_4)_2HPO_4$, and mixtures thereof.

20. The method of claim 1, wherein the hydrophilic ionic liquid is 1-butyl-3-methylimidazolium chloride.

* * * * *